United States Patent
Stephenson et al.

(10) Patent No.: US 7,674,624 B2
(45) Date of Patent: Mar. 9, 2010

(54) METHOD FOR REAL-TIME DETERMINATION OF VOLUME FRACTIONS OF A PRODUCTION FLUID IN A HYDROCARBON RESERVOIR

(75) Inventors: Kenneth E. Stephenson, Newtown, CT (US); Lalitha Venkataramanan, Stamford, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 927 days.

(21) Appl. No.: 10/454,138

(22) Filed: Jun. 4, 2003

(65) Prior Publication Data

US 2004/0248314 A1 Dec. 9, 2004

(51) Int. Cl.
*G01N 33/24* (2006.01)
(52) U.S. Cl. .................. 436/28; 436/148; 73/19.05
(58) Field of Classification Search .................. None
See application file for complete search history.

(56) References Cited

U.S. PATENT DOCUMENTS

| | | | |
|---|---|---|---|
| 6,490,916 B1 | 12/2002 | Goodwin et al. | 73/152.58 |
| 6,561,042 B1 * | 5/2003 | Chen | 73/861.04 |
| 6,823,271 B1 * | 11/2004 | Foss | 702/50 |
| 2004/0010374 A1 | 1/2004 | Raghuraman et al. | 702/13 |

FOREIGN PATENT DOCUMENTS

WO   WO 00/68652   11/2000

OTHER PUBLICATIONS

"Differential Pressure Flowmeters", Nov. 20, 2000, http://www.omega.com/literature/transactions/volume4/T9904-07-DIFF.html.*
"Pressure/Density Level Instrumentation", Oct. 18, 2000, http://www.omega.com/literature/transactions/volume4/T9904-12-PRESS.html.*
Demyanov and Dinariev, "Modeling of multicomponent multiphase mixture flows on the basis of the density-functional method", Fluid Dynamics, 2004.*
Gharbi et al. "Neural network model for estimating the PVT properties of Middle East crude oils", MEOS : Middle East oil show & conference No. 10, Bahrain, 1997, pp. 151-166.*
Al-Shammasi et al. "Bubble point pressure and oil formation volume factor correlations" SPE Middle East oil show & conference No. 11, Bahrain, 1999, pp. 241-256 (38 ref.).*
Bikbulatove et al. "Flowing bottom-hole pressure calculation for a pumped well under multiphase flow", http://arxiv.org/ftp/physics/papers/0504/0504083.pdf.*

(Continued)

*Primary Examiner*—Yelena G Gakh
(74) *Attorney, Agent, or Firm*—Helene Raybaud; James McAleenan; Brigid Laffey

(57) ABSTRACT

A preferred method for determining the flow fraction of a mixture of water, gas and oil in a hydrocarbon reservoir includes measuring pressure and density of the mixture over time, determining a function which approximates a relationship between the density and pressure measurements, calculating a derivative of the function over time, and determining flow fraction based, in part, on the derivative. Preferably, transient data points are eliminated and the remaining set of data points are weight averaged to improve signal to noise ratio. Bubble point pressure, bubble point density and molecular weight and density of the liquid portion of the mixture are also used in the determination.

27 Claims, 9 Drawing Sheets

OTHER PUBLICATIONS

EnSys-Yocum "Multiphase technology", 2003, http://www.ensysenergy.com/EYI%20Files/EYI_PVTMeter.Overview.pdf.*

MPFAT Description, Dec. 2000, http://www.scisoftware.com/products/mofat_details/mofat_details.html.*

"PVT properties of oil, gas, and water add-in for Microsoft Excel": http://www.cgrpttc.Isu.edu/products/pvt/pvtdoc.pdf.*

An et al. "Effects of density and viscosity in vertical zero net liquid flow", J. Energy Resources Technology, Jun. 2000, v. 122, pp. 49-55.*

Zhang et al., "Investigation of oil-air two-phase mass flow rate measurement using Venturi and void fraction sensor", J. Zhejiang University Science, 2005, v. 6A, No. 6, pp. 601-606.*

Bikbulatove et al. "Flowing bottom-hole pressure calculation for a pumped well under multiphase flow", http://arxiv.org/ftp/physics/papers/O504/0504083.pdf, published on-line in Apr. 2005.*

Danesh, Ali. PVT and Phase Behavior of Petroleum Reservoir Fluids. *Elsevier*. (1998) pp. 141-145.

Press et al. Numerical Recipes in C—The Art of Scientific Computing. *Cambridge University Press* (1986) pp. 656-661.

Ali Danesh, "PVT and Phase Behaviour of Petroleum Reservoir Fluids", Copyright © 1998 Elsevier BV.

* cited by examiner

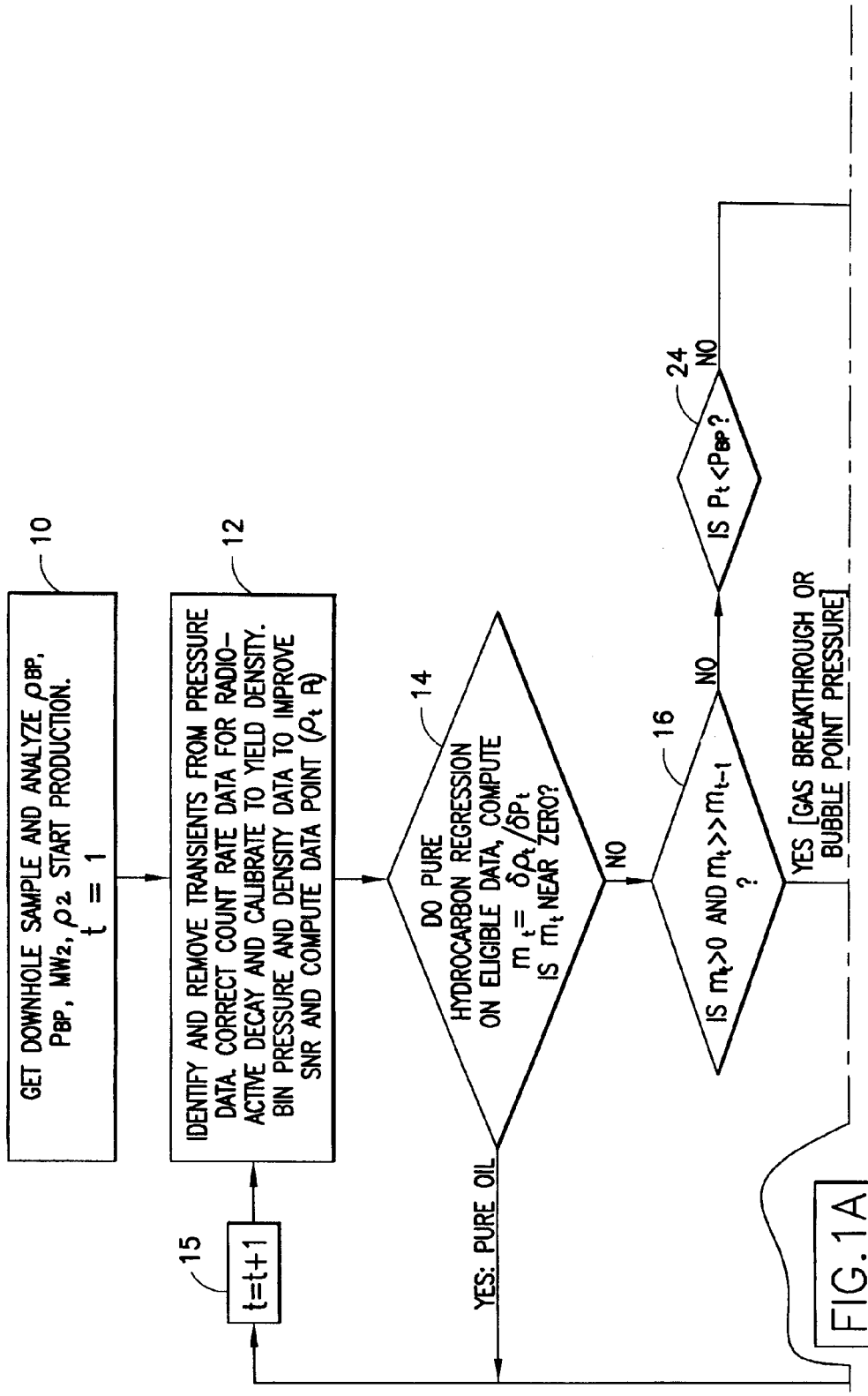

METHOD FOR REAL-TIME DETERMINATION OF VOLUME FRACTIONS OF A PRODUCTION FLUID IN A HYDROCARBON RESERVOIR

BACKGROUND OF THE INVENTION

1. Field of the Invention

This invention relates broadly to the hydrocarbon industry. More particularly, this invention relates to methods and apparatus for the real-time interpretation of data from a downhole flow meter for multiphase mixtures in a hydrocarbon well.

2. State of the Art

The measurement of oil, water, and gas flow rate in each producing zone of an oil well is important to the monitoring and control of fluid movement in the well and reservoir. In addition to a flow meter, each zone may have a valve to control the fluid inlet from that zone. By monitoring flow rates of oil and water from each zone and reducing flow from those zones producing the highest water cut (i.e., ratio of water flow rate to total flow rate), the water production of the entire well can be controlled. This allows the reservoir oil to be swept more completely during the life of the well. In addition, by monitoring flow rates of oil and water from particular zones, zonal allocation of the oil production can be controlled.

Ideally, a flow meter in such an installation should satisfy several criteria:

1) it should be extremely reliable and operate for years at downhole temperatures and pressures;
2) it should operate in both stratified (near-horizontal) and dispersed flow regimes over a wide range of total flow rate and cut;
3) it should not require that the completion be oriented azimuthally in any particular way during installation;
4) it should not require licensing of radioactive sources; and
5) it should allow small changes in water cut and flow rate to be detected.

Co-owned British Patent GB2351810 (International Publication Number WO 00/68652), the complete disclosure of which is hereby incorporated by reference herein, discloses a method and apparatus for determining the flow rates of fluid phases in a pipe containing multiple fluid phases (e.g. oil, water, and gas). A Venturi is provided to measure total volumetric flow rate measurement and a holdup measurement is taken at a location 0-20 (and preferably 3-10) pipe diameters downstream of the Venturi. In a producing well, the volume fraction of a specific fluid phase in the upward moving flow stream is called "holdup" (e.g., water holdup, oil holdup). The relative quantities of the fluids produced at the surface are related to the holdup and upward velocity of each phase. The holdup measurement is made at a downstream location where a substantial amount of mixing occurs and the difference between the velocities of the fluid phases can effectively be ignored. The flow rates of the phases can thus be determined directly from the holdup measurements. The apparatus disclosed is referred to as the "Flow Watcher Densitometer" or "FWD" (a trademark of Schlumberger).

Prior art FIG. 7 is a schematic view of the FWD. The FWD combines a Venturi 110 with a simple gamma-ray attenuation density measurement. A differential pressure sensor 130 measures the pressure drop between the inlet 112 (at port 132) and the Venturi throat 116 (at port 134). A flow instability develops as the flow exits from the Venturi diffuser 118. A source of gamma-rays 142 is provided which is preferably $^{133}$Ba, (although $^{137}$CS or other isotopes can also be used). A gamma-ray detector 144, preferably an NaI (Tl) scintillation detector, is placed diametrically opposite the source 142. The gamma-ray source 142 and detector 144 are preferably placed at a particular location which is a distance 0-20 times (and preferably 3-10 times) the downstream pipe diameter 124. With no fluid in the pipe, gamma-rays from the source travel across the pipe and are detected in the gamma-ray detector with a certain rate $R_s$. With fluid in the pipe, the gamma-rays are scattered and absorbed according to the density of the fluid, with the result that the detection rate R is reduced according to Equation (1) for typical borehole fluids:

$$R = R_s e^{-\tau \rho d} \qquad (1)$$

where d is the diameter of the pipe, $\rho$ is the average density of fluid along the path between source and detector, and $\tau$ is the mass attenuation coefficient, which is essentially constant.

Equation (1) may be used to calibrate the device (i.e., determine $R_s$) with a known fluid such as water. Thus, the average oil holdup or water holdup of a mixture of oil and water along the attenuation path of the gamma-rays (across the diameter of the pipe) can be calculated from the mixture density. This holdup, which is the average along the attenuation path, is equal to the pipe area averaged holdup because the oil and water are mixed relatively thoroughly throughout the pipe cross-section. It has been found on the basis of flow loop experiments that this condition is satisfied approximately 3-10 pipe diameters downstream of the downstream end of the Venturi diffuser even if the flow entering the Venturi is stratified. However, a substantial improvement in the accuracy of determining the relative flow rates of water and oil can be obtained under some circumstances by measuring the holdup at any location from just downstream of the Venturi to about 20 pipe diameters away. For example, it may be sufficiently accurate to measure the holdup at locations where the stratification has been significantly perturbed.

Thus, the FWD combines a Venturi with a gamma ray mixture density measurement at a particular spacing downstream from the Venturi. Over a wide range of flow rates, the spacing assures a well mixed flow with essentially no slip between oil, water or gas phases. This is a major improvement over most other downhole flow meters because no slip-model is needed to translate measured holdup into cut. In two-phase conditions, either gas/liquid or water/oil, the gamma ray measurement (properly calibrated) will provide cut directly and, when combined with the Venturi ΔP measurement, will provide individual-phase flow rates. The interpretation of three-phase flow is more complicated, however.

SUMMARY OF THE INVENTION

It is therefore an object of the invention to provide methods for interpreting three-phase flow using a combination Venturi/gamma ray type device.

It is also an object of the invention to provide methods for interpreting data from the FWD or a similar tool in real time.

It is another object of the invention to provide methods for extracting flow fraction and fluid property information from downhole measurements of mixture density and absolute pressure.

It is a further object of the invention to provide methods and apparatus for measuring the bubble pressure and density of a hydrocarbon fluid.

Another object of the invention is to provide methods and apparatus for identifying the time of first water entry into a hydrocarbon well.

An additional object of the invention is to provide methods and apparatus for identifying the time of gas cap breakthrough into a hydrocarbon well.

A further object of the invention to provide methods and apparatus for calculating the phase cuts in one, two, and three-phase flows.

It is still another object of the invention to perform all of the above methods in real time with the aid of a digital computer.

In accord with these objects which will be discussed in detail below, a method for interpretation of three-phase flow is provided. The method includes, at the start of production and thereafter, periodically making pressure and density measurements, preferably with an FWD tool. Changes in the density ρ and inlet pressure P of the fluid are monitored over time to identify water and gas breakthrough and three-phase cut. In particular, regions of stable well operation with flow rates sufficiently high to give good mixing are identified using Venturi pressure data. The gamma ray count rate is corrected for radioactive decay and calibrated to yield density. The data are subsequently accumulated and weighted-averaged ("binned") to yield representative data points $(\rho_t, P_t)$ at time instant t. The time frame considered for weighted-averaging (such as half a day or a day) is a function of the maximum allowable change in pressure in the time frame and noise statistics of the gamma ray data.

The methods of the invention are based on the knowledge that above the bubble point pressure, a pure hydrocarbon mixture has a near-zero (on the negative side) slope $m_t$ in the density-pressure graph and a positive slope below the bubble pressure. From data points identified as pure hydrocarbon (i.e., oil and gas), the chi-square fit is minimized to simple regression models and a slope $m_t$ and its statistical error $\delta m_t$ at time t are estimated. At each time instant, relevant determinations of water-entry, gas-entry or knee (slope discontinuity) in the density-pressure graph are made by monitoring $m_t$ or suitable functions of $m_t$ over time.

By tracking the slope in the density-pressure graph, particular regimes in which the production fluid is being produced may be tracked. In regime 1, the well is operating above the bubble point pressure and typically, only oil is being produced. In regime 2, the well is operating below the bubble point pressure. In this regime both oil and gas are being produced and it is possible to estimate the oil and gas cut at each time instant given bubble point pressure, bubble point density, as well as the density and molecular weight of the separated liquid. Regime 3 is a regime where water entry has been detected and the three-phase cut can be estimated in real time.

The apparatus of the invention is preferably an FWD apparatus modified to accomplish the methods of the invention. The methods and apparatus of the invention will be described in further detail below with reference to a flow chart and graphs.

DETAILED DESCRIPTION OF THE PREFERRED EMBODIMENTS

Figure 1B:
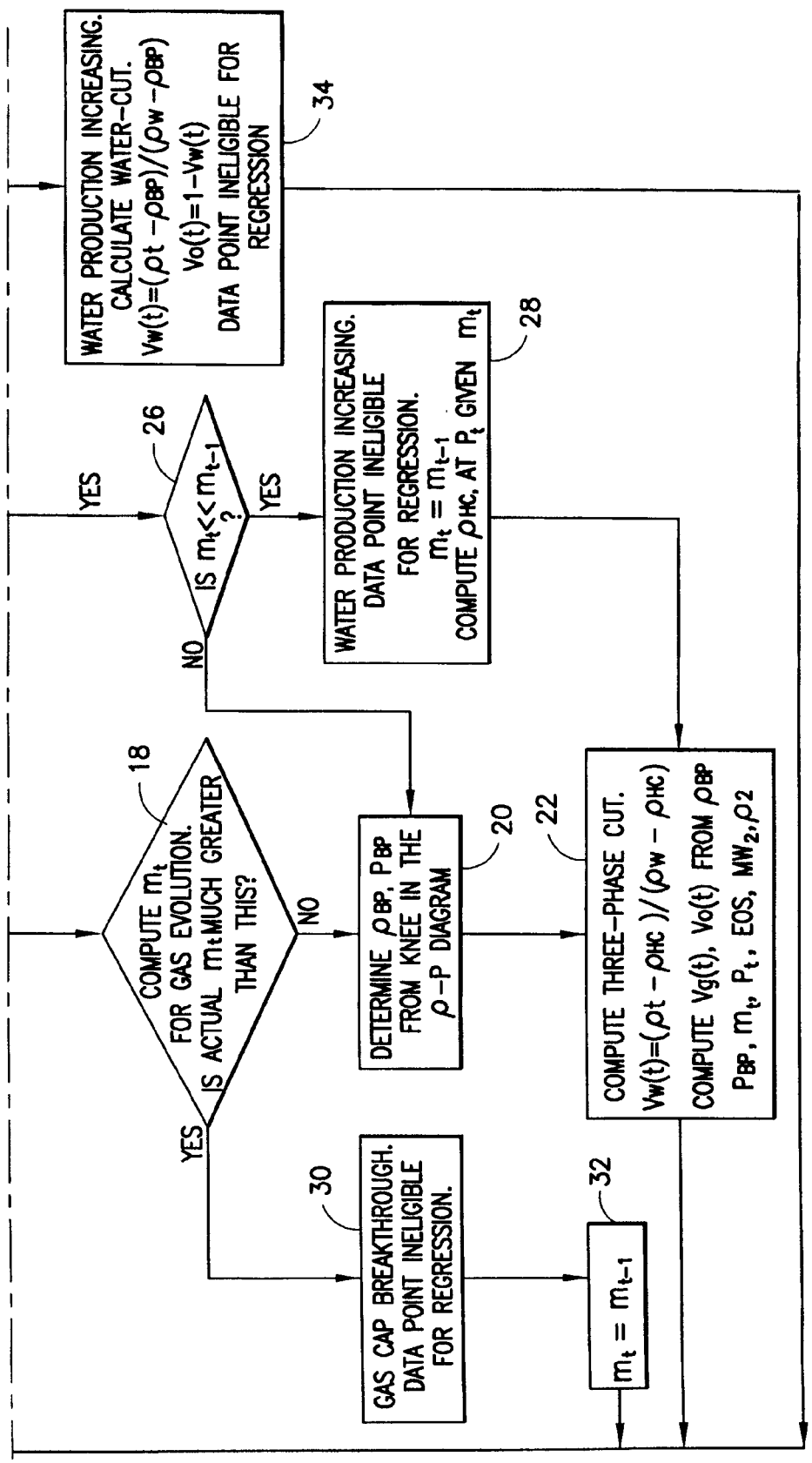
FIG. 1 is a high level flow chart illustrating the methods of the invention.

Before turning to the Figures, it is useful to describe in more detail the above-mentioned flow regimes in which fluids are produced from a formation.

Regime 1:

In this regime, the well is producing above the bubble point pressure. The slope $m_t$ in a density-pressure graph (e.g. FIGS. 3 and 4) at each instant t is obtained by a regression fit on all the other "eligible" data points acquired up until time t. A data point is considered to be eligible for regression if it is not identified (such as by flagging) as an indicator of water-entry. The regression fit to estimate $m_t$ can be a simplistic linear model. In regime 1, the slope is near zero as seen on the right sides of the graphs in FIGS. 3 and 4.

In certain circumstances, while the well is producing oil above the bubble point pressure, water may also be produced. A statistically significant negative value of $m_t$ is indicative of increasing water production (i.e. an increasing density with decreasing pressure). Assuming that the hydrocarbon density is constant above the bubble point pressure, the water-cut at time t, $V_W(t)$, can be estimated from the known bubble point density $\rho_{BP}$ according to $$V_W(t)=(\rho_t-\rho_{BP})/(\rho_W-\rho_{BP}) \qquad (2)$$

where $\rho_w$ is the density of water (i.e. 1000 kg/m$^3$) and $\rho_t$ is the measured density at time t. If desired, a correction for the slight compressibility of liquid hydrocarbon fluid can be made using the corrected density instead of the bubble point density. In this case, oil cut is the remainder, i.e. $V_o(t)=1-V_w(t)$.

Regime 1 to Regime 2 Transition:

A statistically significant positive value of $m_t$ is indicative that the well is in an intermediate regime between regimes 1 and 2 and is passing below the bubble point pressure. The knee in the curve can be used to estimate the bubble point pressure and density. If the initial production has been water-free, then the bubble point density can be estimated by fitting a straight line through the data above bubble point pressure. Since compressibility of oil and water are very small, the slope of this line can be constrained to be zero or close to zero. The intercept of this fitted line provides the bubble point density.

Regime 2:

In this regime, the well is operating below the bubble point pressure. In the context of parametric regression, here a data point is "eligible" for fitting as pure hydrocarbon (including liquid and gas that has come out of solution) if it is not identified flagged either as water production or gas-cap breakthrough. The slope $m_t$ is computed at each time instant by performing a parametric fit on eligible data points below the bubble point pressure acquired up until time t. Volume fractions of oil and gas denoted by $V_O(t)$ and $V_g(t)$ at time t can be computed from $\rho_{BP}$, $P_{BP}$, $MW_2$, $\rho_2$, $P_1$ and the Equation of State as described in more detail below with reference to FIG. 1. Those skilled in the art will appreciate that the "Equation of State" is a function that provides thermodynamically consistent data on the configurational properties of liquids and gases. It is an empirically-derived function which provides a relationship between pressure, density, temperature, and for mixture compositions. As an example, one skilled in the art may use the Peng-Robinson equation of state as described in "PVT and Phase Behavior of Petroleum Reservoir Fluids" by Ali Danesh, Elsevier, 1998.

Regime 2 to Regime 3 Transition:

A water entry point is identified when $m_t$ is significantly decreasing. This can be identified by monitoring a function(s) of $m_t$ that track(s) statistical change in $m_t$. Examples of such functions are $$f_1(t) = (m_t - m_{t-1})/\delta m_{t-1} \quad (3)$$

$$f_2(t) = Q((N-2)/2, \chi_t^2/2) \quad (4)$$

$$f_3(t) = \delta \chi_t^2 / \delta m_t \quad (5)$$

where $\chi_t^2$ refers to the statistical chi-square for observed values of $m_t$, $\delta$ refers to the differential operator, Q refers to the incomplete gamma function and N denotes the number of points at time t. More particularly, a statistical change may be defined when $f_1(t) < -3$, $f_2(t) < 0.1$, or $f_3(t) > \tau_1$, where $\tau_1$ refers to a positive threshold, which can be user defined or computed from statistical error on $f_3(t-1)$. In the case of a water entry point, the water-cut is given by $$V_W(t) = (\rho_t - \rho_t^{HC})/(\rho_W - \rho_t^{HC}) \quad (6)$$

where $\rho_t^{HC}$ is the density of the hydrocarbon mixture estimated from the regression analysis at pressure $P_t$.

A negative water-cut determination from Equation (6) is indicative of a gas-cap breakthrough. Gas-cap breakthrough can also be identified when $m_t$ is significantly greater than that expected from the regression analysis using Equations (3), (4) or (5), i.e. when $f_1(t) > 3$, $f_2(t) < 0.1$, or $f_3(t) < \tau_2$ where $\tau_2$ refers to a negative threshold. This threshold can be user defined or computed from statistical error on $f_3(t-1)$.

Regime 3:

Regime 3 occurs when there is a change in slope such that the slope decreases during regime 2, typically indicating water entry (i.e., three phase flow). In this regime, the well has been operating for some time above and some time below the bubble point pressure. If present, the classical "knee" in the density pressure graph can be used to estimate the bubble point pressure and bubble point density. This knee in the curve can be identified when the data are inconsistent with the regression fits in regimes 1 or 2. In regime 3, three-phase cut can be calculated from Equation (6) and the Equation of State.

Those skilled in the art will appreciate that the term "gas breakthrough" refers to the entry of gas vapor into the well from a multiphase region of the formation. Because of the much greater mobility of gas compared to liquid oil, gas may move much faster toward a well than the reservoir liquid with which it was in thermodynamic equilibrium. Gas breakthrough also has a signature of positive $m_t$ and can be distinguished from gas evolution from solution due to the release of gas from well fluids as the well pressure decreases below the bubble point. In the case of gas breakthrough, the magnitude of $m_t$ is much larger than that expected for gas evolution. It follows in a straightforward manner that the transition through the bubble point pressure can also be easily monitored by identifying when the well goes from regime 1 to regime 2.

FIG. 1 is flowchart for interpretation of three-phase flow in the three regimes. In a preferred embodiment of the invention, at 10, a downhole sample of hydrocarbon fluid is obtained and analyzed for bubble point pressure $P_{BP}$, bubble point density $\rho_{BP}$, density of the separated liquid $\rho_2$, and molecular weight of the separated liquid $MW_2$. This sampling and analysis is preferably performed prior to the start of production, although it is not a required step. Typically, the data is obtained from a nearby well using a tool such as the Schlumberger MDT. (See, e.g. U.S. Pat. No. 6,490,916.) Also at 10, production is started (i.e., t=1) and data acquisition with the Schlumberger FWD or similar device is begun. At 12, transients are identified and removed from the pressure data (as disclosed in co-owned U.S. Ser. No. 10/442,216 to Raghuraman et al., filed on May 20, 2003 and entitled "Processing and Interpretation of Real Time Data from Downhole and Surface Sensors" which is hereby incorporated by reference herein in its entirety); count rate data for radioactive decay is corrected and calibrated to yield density; pressure and density data are binned to improve signal to noise ratio; and the data point $(\rho_t, P_t)$ is computed. It will be appreciated that the analyses performed at 12 assume that $t >> 1$, i.e. that a substantial quantity of data has been accumulated so that statistically significant determinations can be made.

A pure hydrocarbon regression is performed on eligible data points, and the slope $m_t = \delta \rho_t / \delta P_t$ is computed at 14. If $m_t$ is near zero (based on statistical significance) as determined at 14 (see also FIG. 3 at pressures above 2414 psi), the flow is pure oil production in regime 1 and no further analysis is performed until a change in slope is noted. Thus, time is incremented at 15 and additional data is collected and analyzed at 12.

Figure 3:
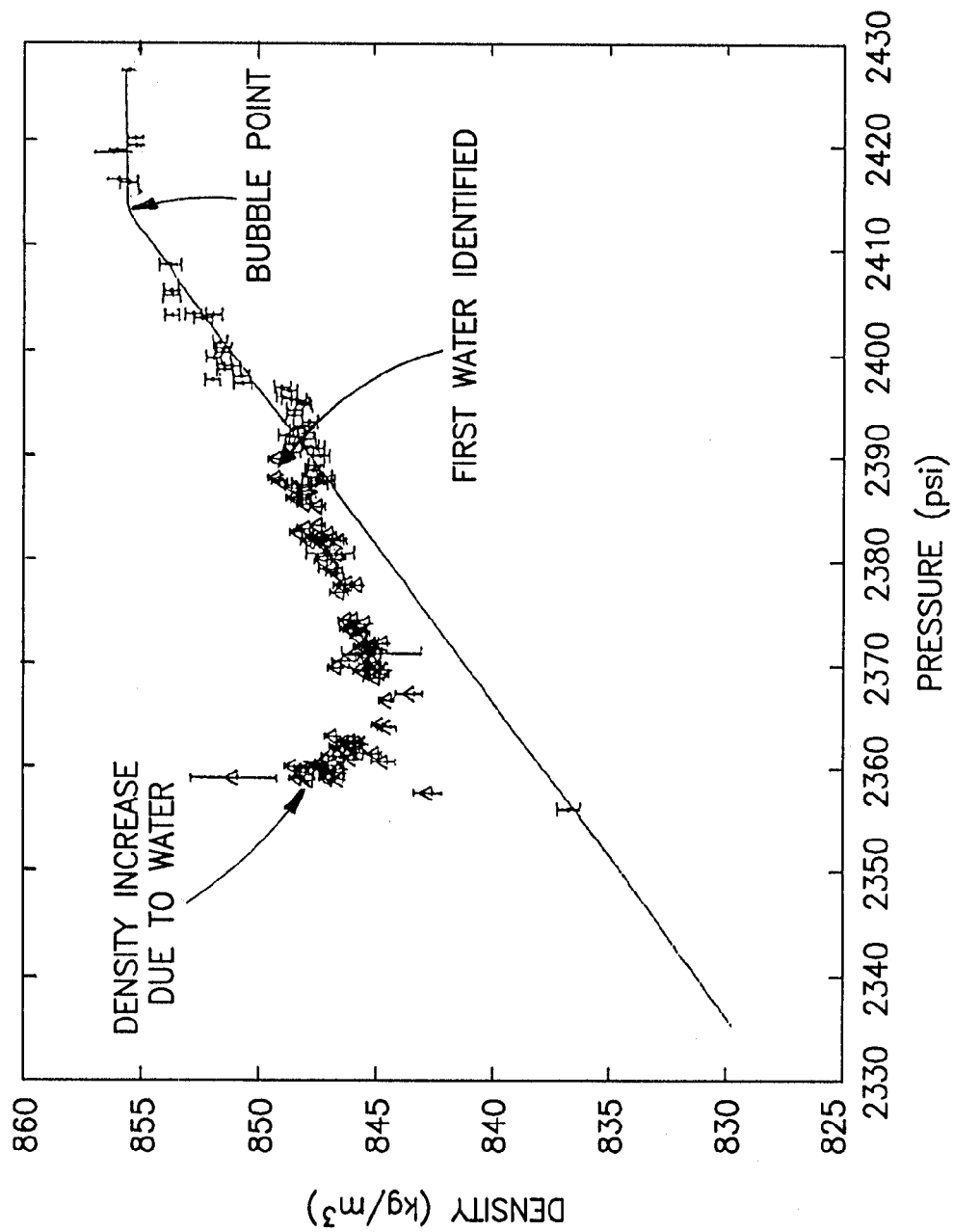
FIG. 3 is a density pressure graph illustrating bubble point measurement and water entry identification.

At some time, it is likely at step 14 that $m_t$ will be found to be greater than zero (see, e.g., FIG. 3 at pressures between about 2390 and 2414 psi). Then a determination is made at 16 as to whether $m_t$ is statistically greater than $m_{t-1}$. If so, an indication has been observed that the bubble point pressure has been reached, or a gas breakthrough has occurred. It will be appreciated that the analysis performed at step 16 may be performed using a suitable function of $m_t$ such as those discussed in Equations 3-5 above. In order to determine whether gas breakthrough has been reached or bubble point pressure has been reached, $m_t$ for gas evolution is computed at 18. If $m_t$ is not much greater than $m_{t-1}$, the well is producing in regime 2 and bubble point pressure and density are determined from the knee in the density pressure graph at 20. After computing bubble point pressure and density at 20, at 22, the volume fractions of oil and gas denoted by $V_O(t)$ and $V_g(t)$ at time t can be computed from $\rho_{BP}$, $P_{BP}$, $MW_2$, $\rho_2$, $P_1$ and the Equation of State. The time is then incremented at 15 and the generation of a next data point is resumed at 12.

It is likely that after stepping through steps 16-22 and updating the time, the next time through, the conditions at 16 will not be met as $m_t$ will not be statistically different from $m_{t-1}$. If that is the case, a determination is then made at 24 as to whether the pressure is below the bubble point (which was determined at step 20). Typically, at this point in production it will be determined at 24 that the pressure is below the bubble point (i.e., the well is now in regime 2), and a determination is made at 26 as to whether $m_t$ is statistically different from $m_{t-1}$. If the slope is not significantly different, this indicates that the well is still producing in regime 2. Then, the bubble point is re-determined at 20 including the latest data in the regression. The bubble point is preferably re-determined each time through this path because the uncertainty in the bubble point determination improves with the additional data. The variance (uncertainty) in the bubble point determination is calculated in the conventional way in least squares regression (see, Press et al., *Numerical Recipes—The Art of Scientific Computing*, Cambridge University Press (1986)). Following step 20, the two-phase cut (oil and gas volumes) is computed at 22. The time is incremented at 15 and more data is accumulated at 12.

Eventually it is possible that a determination will be made at step 26 that the slope of $m_t$ has in fact significantly decreased (see, e.g., the change in slope in FIG. 3 at about a pressure of 2388 psi). In this case, water production has started and the well is said to be producing in regime 3. Then, at 28, the data point is marked ineligible for regression; the previous slope is substituted for the present slope; and the density of the hydrocarbon mixture at $P_t$ given the slope is calculated. The time is incremented at 15 and the generation of data points is resumed at 12.

It is also possible that at some point in time while in regime 2 or regime 3, a determination will be made at step 16 that the slope is greater than zero and statistically larger than the previous slope (see, e.g., the change in slope in FIG. 4 at about a pressure of 2348-2355 psi). If this determination is indicative of a gas cap breakthrough, then at step 18 the actual $m_t$ will be statistically significantly greater than the computed $m_t$ for gas evolution. When gas cap breakthrough is indicated, the data point is marked ineligible at 30. The previous slope $m_{t-1}$ is substituted for the current slope $m_t$ at 32. The time is incremented at 15 and the generation of a next data point is resumed at 12. Gas cap breakthrough is graphically illustrated in FIGS. 2a and 2b which are described in more detail below.

Figure 4:
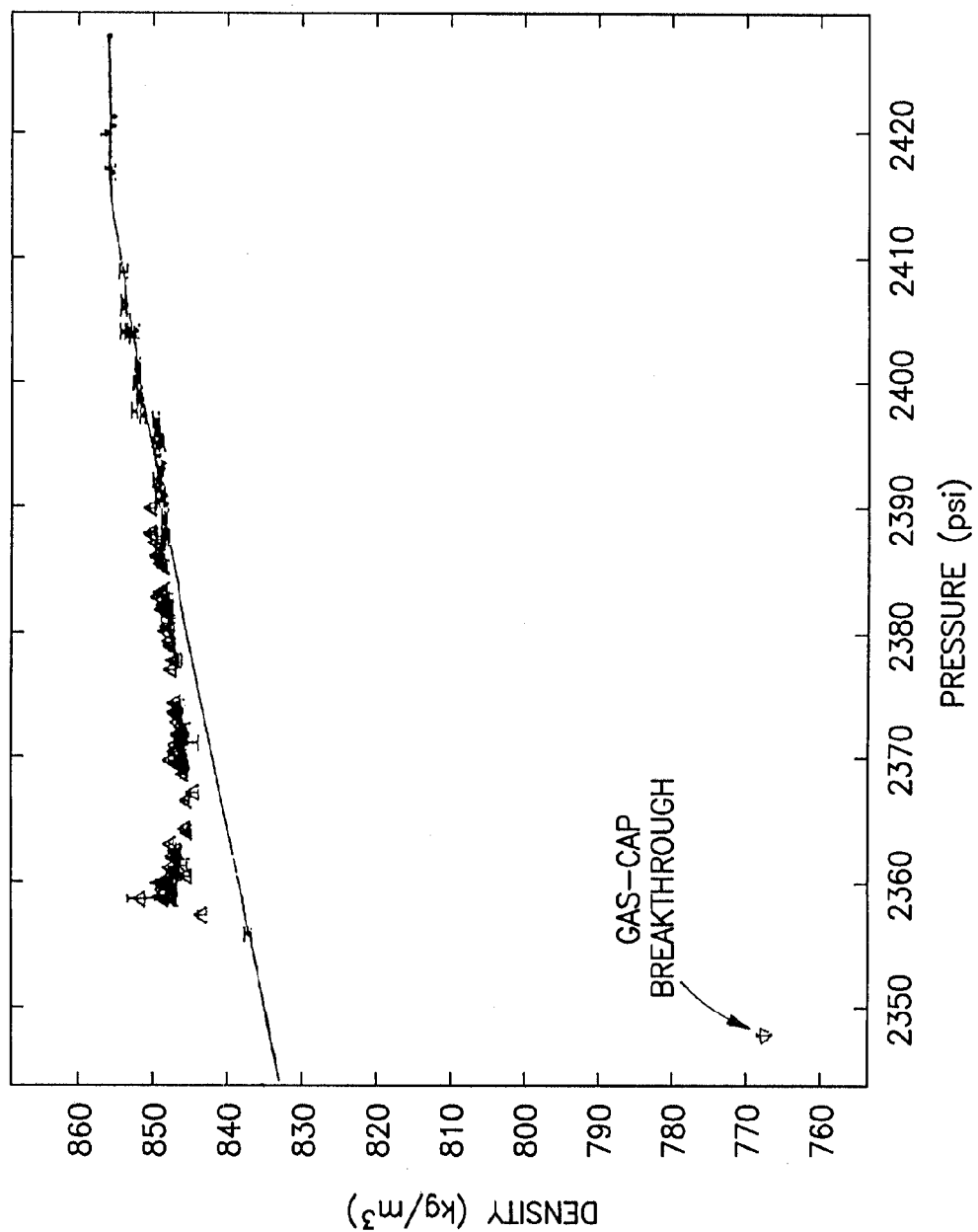
FIG. 4 is a density pressure graph illustrating bubble point measurement and gas breakthrough and water entry identification.

A possible condition which is not illustrated in the graphs of FIGS. 3 and 4 is where it is determined at 24 that the pressure is above the bubble point when the conditions at 16 are not both met. This would occur, for example, if the slope changed from near zero to a negative slope, and would indicate water production at high pressure in regime 1. In this case, the water cut and oil cut are computed at 34 and the data point is marked ineligible for regression. The time is incremented at 15 and data collection continues at 12.

Figure 2A:
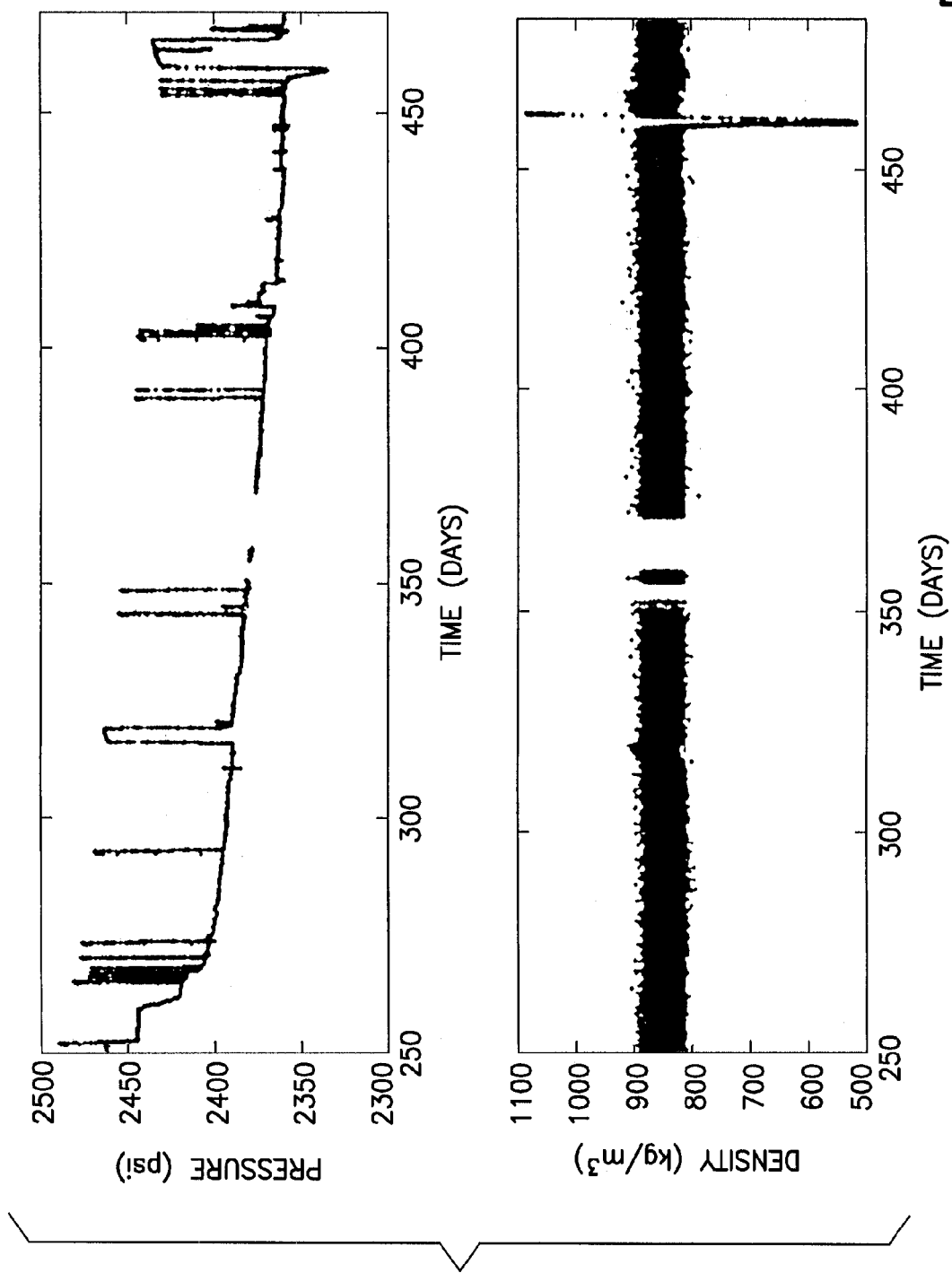
FIG. 2A is a graph of Venturi inlet pressure and density raw data over time.
Figure 2B:
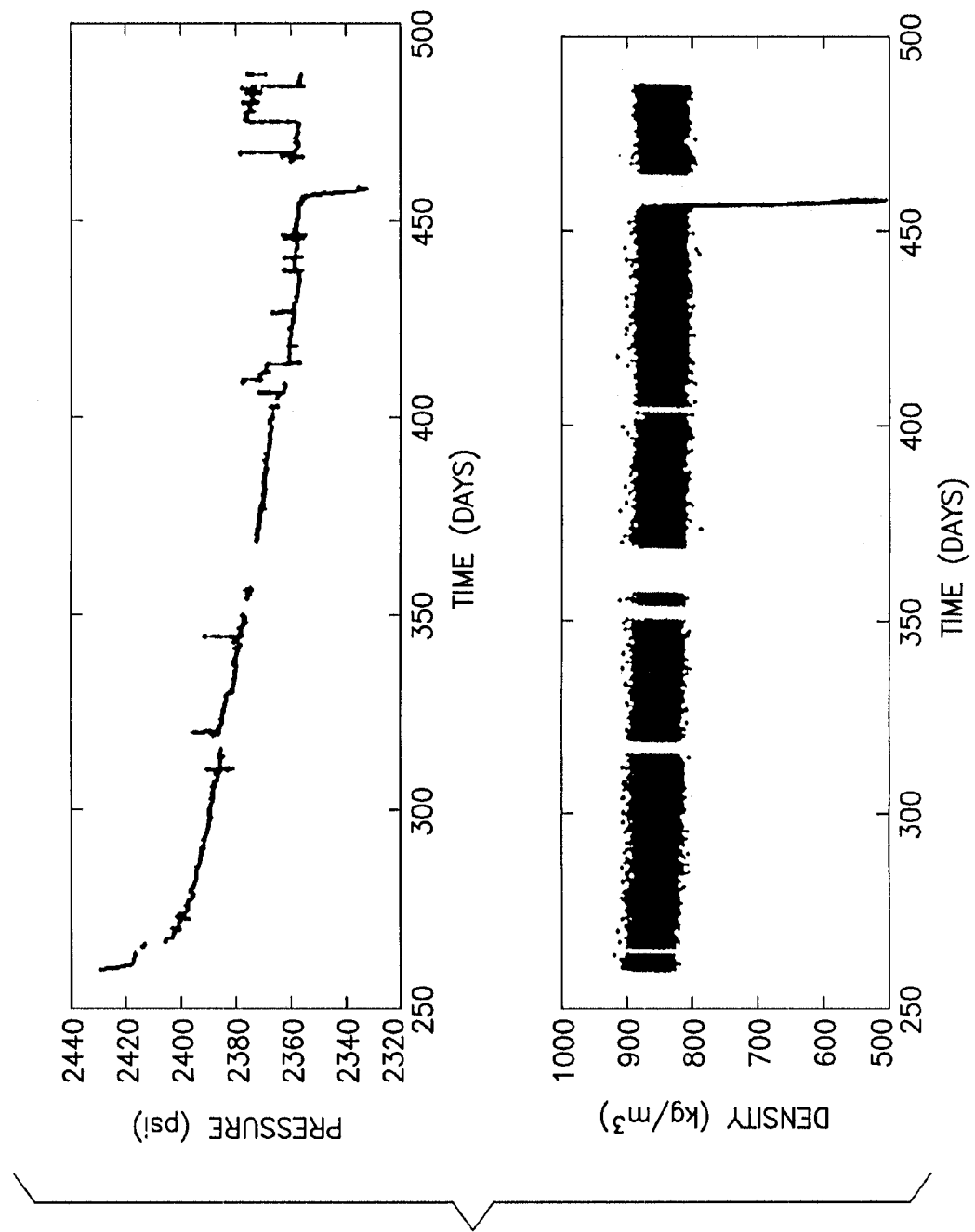
FIG. 2B is a graph of pressure and density data over time after transient removal.

The data illustrated in FIGS. 2a and 2b were acquired in a field test where the FWD was installed at a deviation of approximately 88 degrees (flow slightly uphill) in the heel of a horizontal well. FIG. 2a shows the pressure and density raw data and FIG. 2b shows pressure and the density data after transient removal for the first eight months of field test operation. The pressure data of FIG. 2a are used for transient analysis (step 12 in FIG. 1). The raw, one minute averaged gamma ray data shown in FIG. 2a have low precision and look relatively featureless without further processing. However, a gas breakthrough due to coning shows up dramatically at day 457 even in the raw data of FIG. 2a.

In FIG. 3, the pressure and gamma ray data have been binned into one day intervals (from right to left) to reduce statistical noise in the gamma ray count. At the start of production, the well was producing pure oil with no free gas at the position of the flow meter. As the pressure drops below the bubble point at the flow meter, the slope in pressure vs. density changes and this is used to identify the bubble point pressure (2414 psi) and density (855 kg/m$^3$). Further operation with mixed oil and gas continues until water entry occurs and the slope in pressure vs. density abruptly decreases. This change is detected and signaled as water entry at about 2390 psi. Finally, free gas enters the well and causes the slope in pressure vs. density to abruptly increase at about 2360 psi. FIG. 4 (which includes the same data as FIG. 3, but on a different scale) illustrates the detection and identification of gas entry at about 2347 psi.

The processes described above can all be completed automatically in real time. The method described processed the field test data stream in simulated real time and identified bubble point passage and water and gas entries as they occurred.

Figure 5:
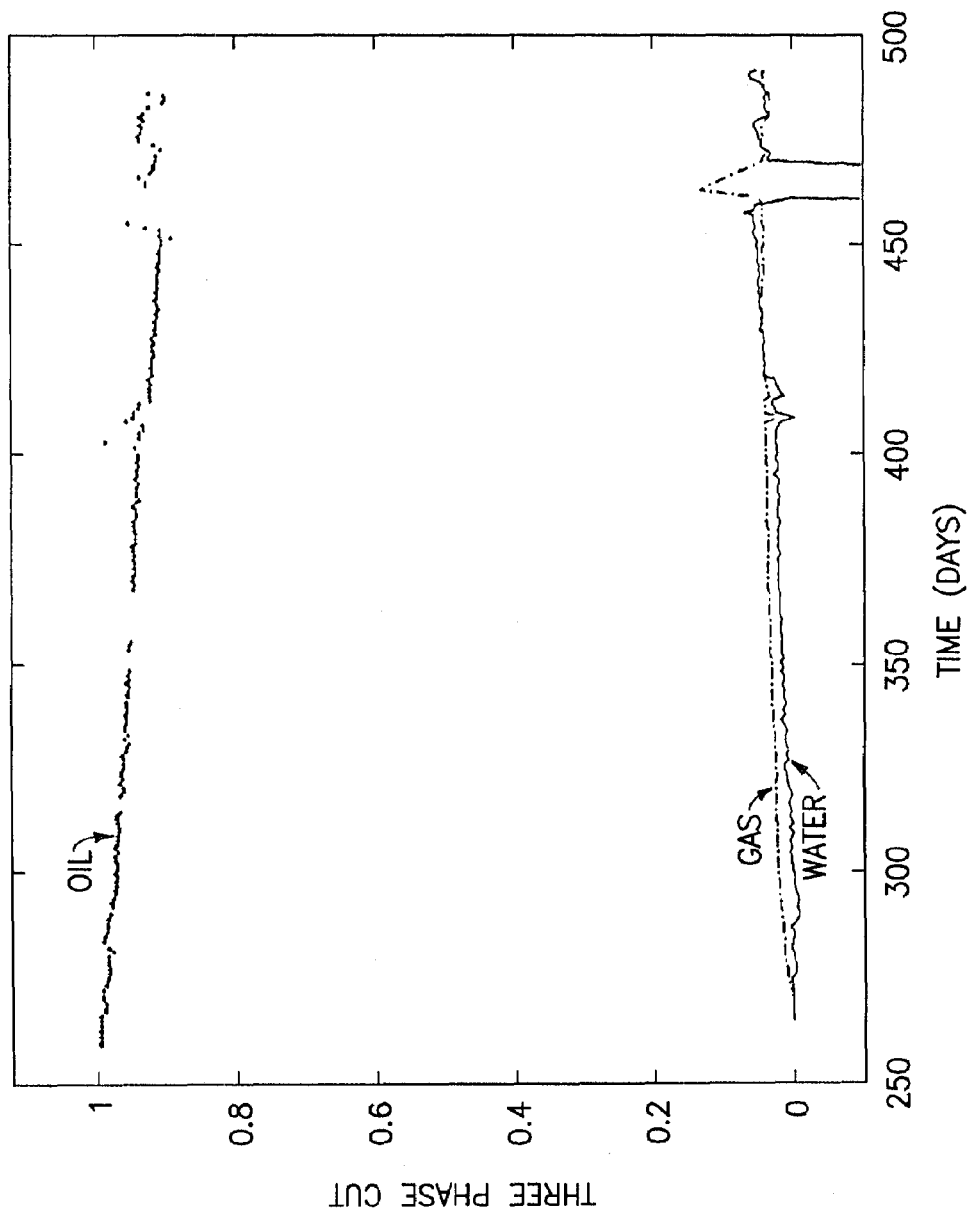
FIG. 5 is a phase cut pressure graph illustrating identification of three-phase cut.

As described above, the absolute pressure and equation of state information can quantify the relative fractions of gas and oil in the hydrocarbon fluid and thereby derive downhole three-phase cuts in real time. FIG. 5 shows the plot of the three-phase cut estimated at each time instant vs. pressure.

Figure 6:
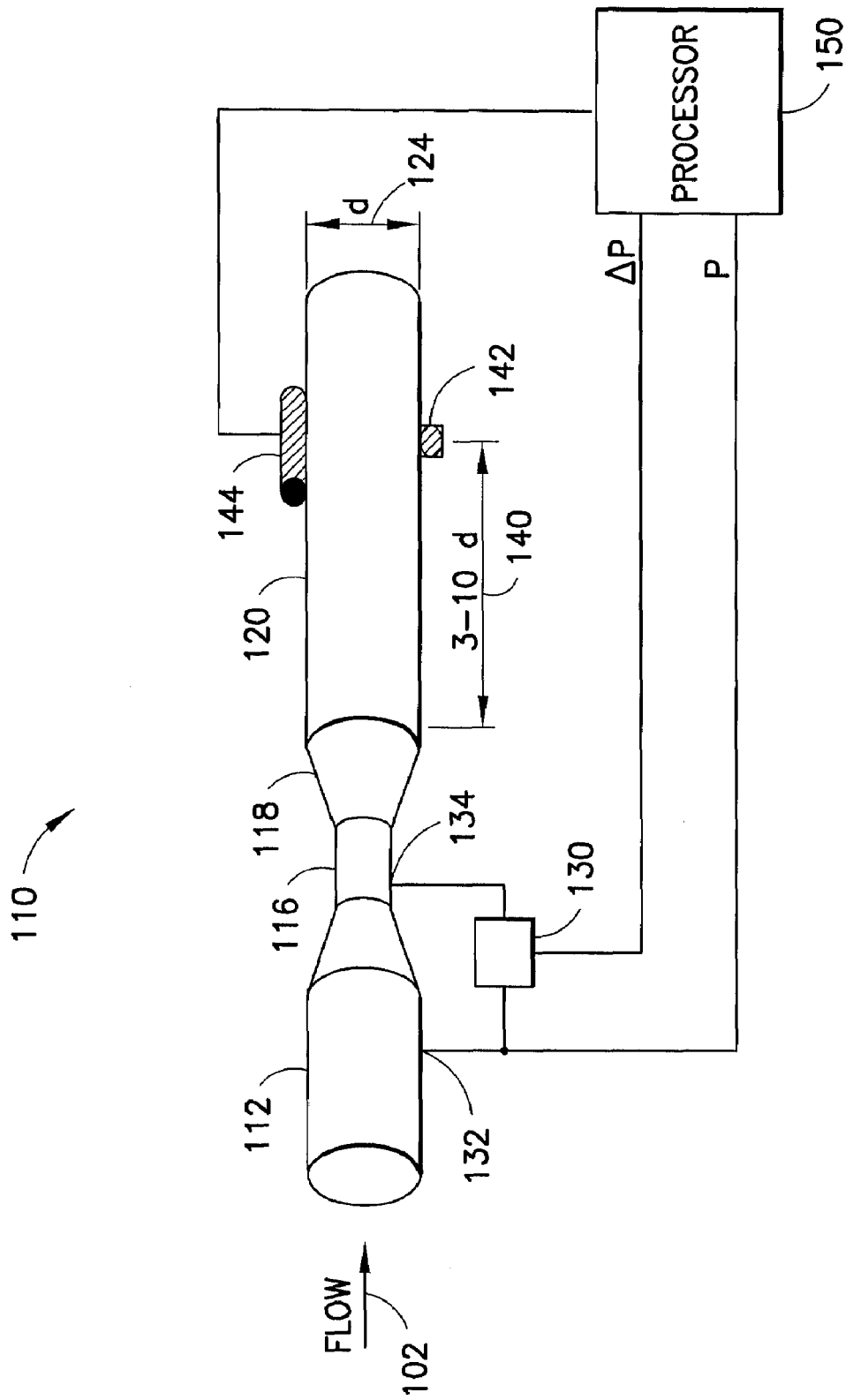
FIG. 6 is an apparatus for performing the methods of the invention.
Figure 7:
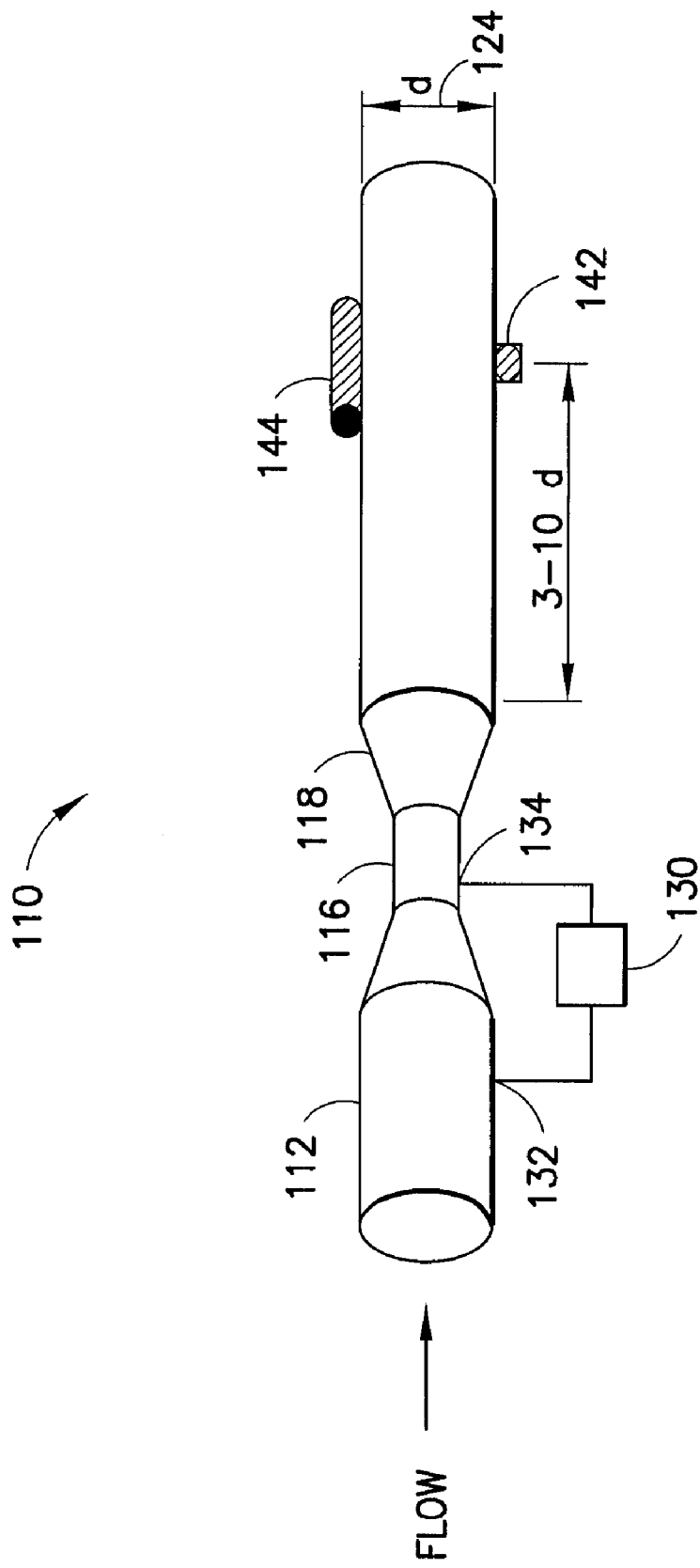
FIG. 7 is a prior art apparatus which can be adapted to perform the methods of the invention.

FIG. 6 illustrates an apparatus for performing the methods of the invention. The apparatus includes the previously described flow meter densitometer 110 coupled to a processor 150. More particularly, the processor 150 receives input from absolute Venturi inlet pressure readings 132, delta (between the inlet and the throat) pressure readings 130 (used for purposes not related to this invention), and the gamma radiation detector 144. The processor 150 may be directly connected to the densitometer 110 and pressure sensor (at 132), or the density and pressure information may be forwarded to the processor via wired or wireless means as are known in the art.

There have been described and illustrated herein methods and apparatus for interpreting Flow Watcher Densitometer data in real time. In particular, methods have been shown for calculating three phase cut, identifying bubble point, gas breakthrough and water entry. While particular embodiments of the invention have been described, it is not intended that the invention be limited thereto, as it is intended that the invention be as broad in scope as the art will allow and that the specification be read likewise. For example, while the first derivative (slope) has been disclosed for interpreting the pressure-density function, higher order derivatives could be used. Alternatively, changes in the pressure-density function values can tracked without using derivatives or by using a combination of different order derivatives. Also, while certain functions for tracking statistical changes were described, and certain values for those functions were disclosed as indicating thresholds for determining significant changes in values, it will be appreciated by those skilled in the art that other functions could be utilized, and that different values could be utilized. Thus, for example, while a "knee" was used in conjunction with a linear model to locate a bubble point, it will be appreciated that where a non-linear model might be used, the bubble point might be identified with a different signature. Further, while particular equipment was disclosed, it will be appreciated that other equipment could be utilized. For example, instead of using a Venturi for mixing, it will be appreciated by those skilled in the art that other types of mixers could be utilized as long as an appropriate density measurement on the multiphase flow can be made. It will therefore be appreciated by those skilled in the art that yet other modifications could be made to the provided invention without deviating from its spirit and scope as claimed.

What is claimed is:

1. A method for real-time determination of volume fractions of production fluid being produced by a hydrocarbon well, comprising:
   a) obtaining pressure and density measurements of the production fluid in situ over time;
   b) applying linear regression analysis to relate said pressure and said density measurements to each other by a linear dependency with a specific slope;
   c) tracking changes in said specific slope in real time; and
   d) determining volume fractions based at least on said changes.

2. The method according to claim 1, further comprising:
   e) prior to obtaining pressure and density measurements of the production fluid, determining bubble point pressure and bubble point density of the production fluid, wherein said step of determining volume fractions is based at least on said bubble point pressure and said bubble point density.

3. The method according to claim 2, further comprising:
   f) prior to obtaining pressure and density measurements of the production fluid, obtaining, not in-situ molecular weight and density of a liquid part of the production fluid, wherein said step of determining volume fractions is based at least on said molecular weight and density of the liquid part of the production fluid.

4. The method according to claim 1, further comprising:
e) determining gas breakthrough based at least on said changes.

5. The method according to claim 4, wherein:
said step of applying linear regression analysis to relate the density and pressure measurements does not use density and pressure measurements obtained during gas breakthrough.

6. The method according to claim 1, further comprising:
e) determining whether water production is increasing based at least on said specific slope.

7. The method according to claim 6, wherein:
said step of applying linear regression analysis to relate the density and pressure measurements does not use density and pressure measurements obtained during increasing water production.

8. The method according to claim 1, wherein:
said step of applying linear regression analysis to relate the density and pressure measurements does not use density and pressure measurements which are transients.

9. The method according to claim 1, further comprising:
e) prior to said step of applying linear regression analysis to relate the density and pressure measurements, weight averaging said density and pressure measurements.

10. The method according to claim 1, wherein:
said step of applying linear regression analysis to relate the density and pressure measurements includes performing a linear regression on selected data points among the pressure and density measurements.

11. The method according to claim 1, wherein:
said real-time determination of volume fractions includes determining water-cut according to the equation $V_W(t) = (\rho_t - \rho_t^{HC})/(\rho_W - \rho_t^{HC})$ where $\rho_t^{HC}$ is the density of the hydrocarbon production fluid estimated from a linear regression analysis at pressure $P_t$.

12. The method according to claim 2, wherein:
said real-time determination of volume fractions includes determining water-cut according to the equation $V_W(t) = (\rho_t - \rho_{BP})/(\rho_W - \rho_{BP})$ where $\rho_w$ is the density of water, $\rho_{BP}$ is the bubble point density, and $\rho_t$ is the determined density at time t.

13. A method for real-time determination of volume fractions of a production fluid in a hydrocarbon reservoir, comprising:
a) obtaining pressure and density measurements of the production fluid in situ over time;
b) applying linear regression analysis to relate said pressure and said density measurements to each other by a linear dependency with a specific slope;
c) tracking changes in said specific slope in real time; and
d) determining whether water production is increasing based, at least on said changes.

14. The method according to claim 13, further comprising:
e) determining gas breakthrough based, at least, on said changes.

15. The method according to claim 13, further comprising:
e) determining bubble point pressure based, at least, on said changes.

16. The method according to claim 15, further comprising:
f) determining whether water production is increasing based, at least, on bubble point pressure.

17. The method according to claim 15, further comprising:
f) determining gas cut and oil cut based, at least, on bubble point pressure.

18. A method for real-time determination of volume fractions of a production fluid in a hydrocarbon reservoir during well production, comprising the steps of:
a) obtaining downhole pressure $P_t$ and density $\rho_t$ measurements for time t;
b) setting t=t+1;
c) repeating steps "a" and "b" a sufficient number of times to permit a first linear regression analysis on said pressure and density measurements;
d) performing a second linear regression on selected data points among the pressure and density measurements;
e) calculating a slope $m_t = \delta\rho_t/\delta P_t$;
f) determining in real time whether the slope is statistically near zero;
g) if the slope $m_t$ is statistically near zero, indicating in real time that the well is producing pure oil; and
h) repeating steps b), and d) through g).

19. The method according to claim 18, further comprising:
i) if the slope $m_t$ is greater than zero and $m_t$ is statistically significantly larger than $m_{t-1}$, determining the bubble point pressure and density from the data accumulated thus far.

20. The method according to claim 19, further comprising:
j) determining the oil and gas phase cuts from the data accumulated thus far, and returning to step h).

21. The method according to claim 18, further comprising:
if the slope $m_t$ is not greater than zero or $m_t$ is not statistically significantly larger than $m_{t-1}$, computing a three phase cut of oil, gas and water from the data accumulated thus far.

22. The method according to claim 21, further comprising:
prior to computing a three phase cut, determining whether the slope $m_t$ is statistically significantly smaller than $m_{t-1}$.

23. The method according to claim 22, further comprising:
if slope $m_t$ is not statistically significantly smaller than $m_{t-1}$,
indicating that water production is increasing,
marking the data point ineligible for first linear regression, and
setting $m_t = m_{t-1}$.

24. The method according to claim 18, further comprising:
i) if the slope $m_t$ is greater than zero and $m_t$ is statistically significantly larger than $m_{t-1}$, computing the slope for gas evolution and comparing it to the actual slope $m_t$;
j) if the actual slope is much greater than the computed slope for gas evolution,
indicating a gas cap breakthrough,
marking the data point ineligible for first linear regression,
setting $m_t = m_{t-1}$; and
k) returning to step h).

25. The method according to claim 18, further comprising:
prior to step a), obtaining a downhole sample and analyzing the downhole sample to determine bubble point density, bubble point pressure, molecular weight of the production fluid, and density of the production fluid.

26. The method according to claim 20, further comprising:
k) refining said determination of said bubble point pressure using additional data obtained.

27. The method according to claim 26, further comprising:
l) calculating a variance in said bubble point pressure determination.

\* \* \* \* \*